(12) United States Patent
Rosenblum et al.

(10) Patent No.: US 9,545,391 B2
(45) Date of Patent: Jan. 17, 2017

(54) MEDICATED OINTMENT FOR TREATING HEMORRHOID AND METHOD OF USING THE SAME

(75) Inventors: Archer Rosenblum, Milllington, NJ (US); John Maurello, Oceanside, NY (US)

(73) Assignee: Hemaway LLC, NY, NY (US)

( * ) Notice: Subject to any disclaimer, the term of this patent is extended or adjusted under 35 U.S.C. 154(b) by 170 days.

(21) Appl. No.: 13/136,159

(22) Filed: Jul. 26, 2011

(65) Prior Publication Data
US 2012/0040019 A1 Feb. 16, 2012

Related U.S. Application Data

(60) Provisional application No. 61/401,273, filed on Aug. 11, 2010.

(51) Int. Cl.
| | | |
|---|---|---|
| *A61K 31/355* | (2006.01) | |
| *A61K 31/167* | (2006.01) | |
| *A61K 36/87* | (2006.01) | |
| *A61K 36/886* | (2006.01) | |
| *A61K 45/06* | (2006.01) | |

(52) U.S. Cl.
CPC .......... *A61K 31/355* (2013.01); *A61K 31/167* (2013.01); *A61K 36/87* (2013.01); *A61K 36/886* (2013.01); *A61K 45/06* (2013.01)

(58) Field of Classification Search
CPC A61K 2300/00; A61K 31/137; A61K 31/167; A61K 9/0014; A61K 31/573; A61K 31/245; A61K 31/192; A61K 9/0031; A61K 9/0034; A61K 31/445; A61K 9/06; A61K 31/00
See application file for complete search history.

(56) References Cited

U.S. PATENT DOCUMENTS

| | | | | |
|---|---|---|---|---|
| 7,022,335 | B2 * | 4/2006 | Hori et al. | 424/433 |
| 7,273,887 | B1 * | 9/2007 | Wepfer | 514/535 |
| 2003/0035850 | A1 * | 2/2003 | Blanco | 424/725 |
| 2006/0275218 | A1 * | 12/2006 | Tamarkin et al. | 424/45 |
| 2007/0148105 | A1 * | 6/2007 | Spector | 424/59 |
| 2008/0003273 | A1 * | 1/2008 | Feldkamp et al. | 424/448 |
| 2009/0169652 | A1 * | 7/2009 | Osborne | 424/727 |
| 2009/0196840 | A1 * | 8/2009 | Lorenzo | 424/59 |
| 2010/0055185 | A1 * | 3/2010 | Agisim et al. | 424/484 |

OTHER PUBLICATIONS

FDA Guidance—OTC Skin Protectants 2008 [downloaded on May 22, 2015 from the website http://www.accessdata.fda.gov/scripts/cdrh/cfdocs/cfcfr/CFRSearch.cfm?CFRPart=347&showFR=1&subpartNode=21:5.0.1.1.23.2].*
Baydar et al., Grasas y Aceites 58: 29-33 (2007).*
Ei-Saied et al., Ernährungswiss 20: 145-151 (1981).*

* cited by examiner

*Primary Examiner* — Sue Liu
*Assistant Examiner* — Thor Nielsen
(74) *Attorney, Agent, or Firm* — Dan De La Rosa

(57) ABSTRACT

This invention relates to an externally applied ointment that aids in relieving irritation, pain or mild inflammation of the skin or mucous membranes associated with hemorrhoids and the method of using such ointment lotion. The formulation of the present invention contains phenylephrine HCl, lidocaine grape skin/seed/leaf extract and aloe plants extract.

9 Claims, No Drawings

MEDICATED OINTMENT FOR TREATING HEMORRHOID AND METHOD OF USING THE SAME

CROSS REFERENCE TO RELATED APPLICATIONS

This application claims priority to U.S. provisional application No. 61/401,273 filed Aug. 11, 2010, which is herein incorporated in its entirety by reference

FIELD OF THE INVENTION

The present invention relates to topical ointments including a local anethstetic and an active ingredient for treating hemorrhoids so as to alleviate the symptoms associated with hemorrhoids. The ointment can be used alone or in combination with other hemorrhoid treating devices and/or medications.

BACKGROUND OF THE INVENTION

This invention relates to topical ointments for treating hemorrhoids to relieve or eliminate pain and discomfort associated with hemorrhoids. More specifically, the present invention relates to topical ointments including lidocaine and phenylephrine HCl and optionally grape leaf extract and aloe extract for the relief of pain and discomfort arising from hemorrhoids (piles) or other related conditions. The present invention is also directed to medicated patches including the composition of the present invention that can be placed on or near the hemorrhoid in order to deliver relief and provide some comfort to the sufferer.

A number of hemorrhoid treating ointments are available on the market today but none include the active ingredients of the present invention at the maximum strengths allowed by the FDA. Therefore, relief form these ointments currently available are short lived and moderate at best. The present invention addresses the shortcomings associated with the ointments available on the market today as well as providing additional benefits.

These features, together with other objects and advantages, which will become subsequently apparent, reside in the details of the composition of the present invention as more fully hereinafter described and claimed.

SUMMARY OF THE INVENTION

The present invention is directed to a cream, ointment or topical lotion for treating hemorrhoids and associated conditions comprising an effective amount of phenylephrine HCl and an anesthetic effective amount of lidocaine all disbursed in a pharmaceutically acceptable topical carrier for relieving swelling, burning, pain, and itching caused by hemorrhoids and associated conditions.

The present invention is also directed to a cream, ointment or topical lotion for treating hemorrhoids and associated conditions comprising an effective amount of phenylephrine HCL, an anesthetic effective amount of lidocaine, an effective amount of *Vitis vinifera* (Grape) skin extract, all disbursed in a pharmaceutically acceptable topical carrier for relieving swelling, burning, pain, and itching caused by hemorrhoids and associated conditions.

The present invention is also directed to a cream, ointment or topical lotion for treating hemorrhoids and associated conditions comprising an effective amount of phenylephrine HCl, an anesthetic effective amount of lidocaine, an effective amount of *Vitis Vinifera* (Grape) skin/seed/leaf extract to reduce inflammation and pain associated with hemorrhoids and associated conditions, and an effective amount of aloe *Barbadensis* leaf juice extract all disbursed in a pharmaceutically acceptable topical carrier for relieving swelling, burning, pain, and itching caused by hemorrhoids.

The present invention is also directed to a method of treating hemorrhoids and associated conditions by applying any one of the compositions described herein according to a prescribed regime or on an as needed basis.

The present invention is also directed to a kit containing a hemorrhoid seat or device to aid in mechanically manipulating the body for treating hemorrhoids and associated conditions in addition to any one or the compositions described herein for aiding in treating hemorrhoids and associated conditions.

These features, together with other objects and advantages of the present composition, method and kit will become subsequently apparent and reside in the details of the composition and it mode of operation as more fully hereinafter described and claimed.

DETAILED DESCRIPTION OF THE INVENTION

Hemorrhoids are one of the most common causes of anal pathology. Subsequently, hemorrhoids are blamed for virtually any anorectal complaint by patients and medical professionals alike. Confusion often arises because the term "hemorrhoid" has been used to refer to both normal anatomical structures and pathological structures. In the context of this application, "hemorrhoids" refers to the pathological presentation of hemorrhoidal venous cushions.

Hemorrhoidal venous cushions are normal structures of the anorectum and are universally present unless a prior intervention has taken place. Because of their rich vascular supply, highly sensitive location, and tendency to engorge and prolapse, they are common causes of anal pathology. Symptoms can range from mildly bothersome, such as pruritus, to quite concerning, such as rectal bleeding, and while it is a common condition diagnosed in clinical practice, many patients are too embarrassed to ever seek treatment. Consequently, the true prevalence of pathologic hemorrhoids is not known.

Hemorrhoidal venous cushions are a normal part of the human anorectum and arise from subepithelial connective tissue within the anal canal. Present in utero, these cushions surround and support distal anastomoses between the superior rectal arteries and the superior, middle, and inferior rectal veins. They also contain a subepithelial smooth muscle layer, contributing to the bulk of the cushions. Normal hemorrhoidal tissue accounts for approximately 15-20% of resting anal pressure and provides important sensory information, enabling the differentiation between solid, liquid, and gas.

Most people contain 3 of these cushions. Although classically described as lying in the right posterior (most common), right anterior, and left lateral positions, this combination is found in only 19% of patients. Hemorrhoids can be found at any position within the rectum.

Hemorrhoids are classified by their anatomic origin within the anal canal and by their position relative to the dentate line. The dentate line is between the simple columnar epithelium of the rectum and the stratified epithelium of the anal canal. Internal hemorrhoids develop above the dentate line from embryonic endoderm. They are covered by the simple columnar epithelium of anal mucosa and lack somatic sensory innervation and are therefore painless.

External hemorrhoids develop from ectoderm and arise distal to the dentate line. They are covered by stratified squamous epithelium and receive somatic sensory innervation from the inferior rectal nerve rendering them painful when irritated.

Mixed hemorrhoids are confluent internal and external hemorrhoids. Internal hemorrhoids drain through the superior rectal vein into the portal system. External hemorrhoids drain through the inferior rectal vein into the inferior vena cava. Rich anastomoses exist between these 2 and the middle rectal vein, connecting the portal and systemic circulations.

Hemorrhoids usually are not dangerous or life threatening. Rarely, a patient can have bleeding so severe, that severe anemia or death may occur. In some cases, hemorrhoidal symptoms simply go away within a few days. But in most cases, hemorrhoidal symptoms eventually return, often worse than they were before. The most common symptom of internal hemorrhoids is bright red blood covering the stool, on toilet paper, or in the toilet bowl. However, an internal hemorrhoid may protrude through the anus outside the body, becoming irritated and painful. This is known as a protruding hemorrhoid. Symptoms of external hemorrhoids may include painful swelling or a hard lump around the anus that results when a blood clot forms. This condition is known as a thrombosed external hemorrhoid. In addition, excessive straining, rubbing, or cleaning around the anus may cause irritation with bleeding and/or itching, which may produce a vicious cycle of symptoms. Draining mucus may also cause itching.

Therefore, what is needed is a medicated ointment/topical cream that not only shrinks the hemorrhoid but also delivers immediate relief to the pain and itching often associated with this condition. The present invention is directed to a medicated hemorrhoid ointment or cream that contains phenylephrine HCl and lidocaine, as well as, homeopathic ingredients such as *Vitis Vinifera* (Grape) skin/seed/leaf extract and aloe *Barbadensis* leaf juice extract ingredients disbursed in a gel or paste. Application of this cream reduces the inflammation associated with hemorrhoids as well as the other symptoms often associated with hemorrhoids and related condition such as itching and pain. While the invention is described in the general context of compositions for treating hemorrhoids it is envisioned that the compositions can be used with conditions related to hemorrhoids as well. This includes but is not limited to anal fissures, piles, abscesses, fistulas and related conditions.

Also, as used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, the term "treatment" refers to the medical management of a patient with the intent to cure, ameliorate, stabilize, or prevent a hemorrhoids and related conditions or disorders. This term includes active treatment, that is, treatment directed specifically toward the improvement of hemorrhoids and related conditions and includes palliative treatment, that is, treatment designed for the relief of symptoms rather than the curing of hemorrhoids and related conditions.

As used herein, the term "alleviate" or "alleviating" refers to lightening or lessening the severity of a symptom, condition, or outbreak of hemorrhoids and related conditions. For example, a treatment that reduces the severity of pain in a subject can be said to alleviate pain.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms associated with hemorrhoids and related conditions, but is generally insufficient to cause adverse side affects. The specific therapeutically effective dose level for any particular patient will depend upon a variety of factors including the severity of the hemorrhoids and related conditions; the specific composition employed; the age, body weight, general health, sex and diet of the patient; the duration of the treatment; drugs used in combination or coincidental with the specific compound employed and like factors well known in the medical arts.

For example, it is well within the skill of the art to start doses of a composition at levels lower than those required to achieve the desired therapeutic effect and to gradually increase the dosage or the amount of applications of the cream until the desired effect is achieved.

As used herein, the term "pharmaceutically acceptable carrier" refers to sterile aqueous or nonaqueous solutions, dispersions, suspensions or emulsions, for reconstitution into steriletopical ointments and/or creams. Examples of suitable aqueous and nonaqueous carriers, diluents, solvents or vehicles include water, ethanol, methanol, isopropanol, polyols (such as glycerol, propylene glycol, polyethylene glycol and the like), carboxymethylcellulose and suitable mixtures thereof, vegetable oils (such as olive oil, light mineral oil, cottonseed oil, castor oil, and the like) and injectable organic esters such as ethyl oleate. Proper fluidity can be maintained, for example, by the use of coating materials such as lecithin, by the maintenance of the required particle size in the case of dispersions and by the use of surfactants.

The term "pharmaceutically acceptable salt" refers to a salt prepared from a base or acid that is acceptable for administration to a patient, such as a mammal. Such salts can be derived from pharmaceutically acceptable inorganic or organic bases and from pharmaceutically acceptable inorganic or organic acids. Salts derived from pharmaceutically acceptable inorganic bases include aluminum, ammonium, calcium, copper, ferric, ferrous, lithium, magnesium, manganic, manganous, potassium, sodium, zinc and the like.

Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maple, malic, mandelic, methanesulfonic, mucic, naphthalenesulfonic, nicotinic, nitric, pamoic, pantothenic, phosphoric, succinic, sulfuric, tartaric (providing a tartrate or bitartrate), p-toluenesulfonic and the like. Particularly preferred are citric, hydrobromic, hydrochloric, maple, phosphoric, sulfuric and tartaric acids.

The terms "anorectal disease", "painful conditions of the anal region", "anal conditions", "anal pain", and the like, are used herein to describe symptoms of discomfort or pain in a person's anorectal area, or the diseases and disorders that produce them. Anorectal diseases include anal fissures, thrombosed or inflamed hemorrhoids, pain associated with the after effects of anal surgery (such as rubber-band ligation of internal hemorrhoids) and chronic anal pain. The anorectal area comprises the anal mucosa, the mucosa of the most distal portion of the rectum, the internal and external anal sphincters, the skin immediately surrounding the anus.

"Active agent", as used herein, refers to any component in a composition of the present invention that increases the analgesic effects of that composition and can be added to the compositions of the present invention to enhance their ability to reduce the symptoms associated with anorectal disease. In the composition of the present invention, .alpha.-blockers, lidocaine and sucralfate are all active agents. "Active agent" is also used to refer to any component in any known composition (e.g. preparation H) that increase the analgesic effects of that composition.

"Active ingredient", differs from the use of "active agent", as used herein, to mean any component that can be added to a composition that has some biological effect, whether the biological effect is directly related to anorectal disease or not. The biological effect is preferably curative. Such components might have analgesic or anesthetic effects, for example, lidocaine, (hydrocortisone and triamcinolone), non-steroidal antiinflammatory drugs (including specifically diclofenac opiates), or salicylates (salsalate, sulfasalazine). Such components might alternatively have an activity unrelated to pain reduction. For example, such active ingredients as antibiotics, antifungals, or antivirals.

"Active compound" as used herein, encompasses both the drugs referred to as "active agents" and the drugs referred to as "active ingredients" defined herein. "Active compound" is used generally to refer to anything with relevant biological activity that is added to biologically inert ingredients in a composition intended for therapeutic use. For example grape seed oil, grape leaf oil and grape skin oils are examples of active compounds used in the present invention.

Xylocaine has the generic name lidocaine and is an active ingredient of the composition of the present invention. Lidocaine is an intermediate-duration anesthetic, that is incorporated into the gel, lotion, paste or solution of the present invention and can be safely applied within an effective dosage protocol topically usually every 3-4 hours to obtain relief of pain. If used, the concentration ranges from as low as approximately 2% to as high as approximately 15%, preferably approximately 5%. Lidocaine is a local anesthetic and antiarrhythmic drug. Lidocaine is used topically to relieve itching, burning and pain from skin inflammations that is often associated with hemorrhoids and related conditions. Together with phenylephrine HCl these two ingredients work to shrink and relieve pain and itching associated with hemorrhoids and related conditions almost immediately. The ointment of the present invention contains the maximum concentration of phenylephrine HCl and lidocaine permitted by the Food and Drug Administration (FDA) which is sufficient for some outbreaks of hemorrhoids but more severe cases may require multiple applications.

The compositions of the present invention can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid, chlorohexidine digluconate, and the like. Antioxidants, such as BHT, can be included. It can also be desirable to include isotonic agents such as sugars, sodium chloride and the like.

The inventors contemplate that any conventional adjuvants can be used in the present composition. These may include antioxidants, for example sodium or potassium metabisulfite; isotonic agents such as sodium chloride; chelating agents such as EDTA or citric acid; pH adjustment agents such HCl or NaOH, present in an amount desirable to achieve a pH of, for example, from 3.3-5.5; minor impurities such as aluminum salts; and other ingredients. Other adjuvants that may find use herein include opiates, such as morphine and fentanyl (used to provide epidural/spinal anesthesia); NMDA antagonists, such as dextromethorphan; clonidine; antiinflammatory agents; antibiotics; and the like. When preparing the pharmaceutical compositions of this invention, the active ingredient is customarily diluted by an excipient. Representative examples of suitable excipients include water, sterile saline, syrup, and methylcellulose. The formulations can additionally include emulsifying and suspending agents; preserving agents, such as methyl- and propylhydroxy-benzoates; and flavoring and coloring agents.

The compounds of this invention may be formulated using conventional techniques such as those described in Remington's Pharmaceutical Sciences, Mace Publishing Co., Philadelphia, Pa. 17th Ed. (1985) and "Modern Pharmaceutics," Marcel Dekker, Inc. 3.sup.rd Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, Advanced Organic Chemistry: Reactions, Mechanisms and Structure, 4th Ed. (New York: Wiley-Interscience, 1992).

In one embodiment of the present invention, the composition designed to treat hemorrhoids and related conditions comprises a therapeutic effective amount of phenylephrine HCl for relieving swelling, burning, pain, and itching caused by hemorrhoids and related conditions. Phenylephrine HCl is an active ingredient of the ointment that acts to shrink the swollen tissues associated with hemorrhoids by constricting blood vessels that feed blood and fluid to the area around the hemorrhoid. Phenylephrine HCl is a α-adrenergic receptor agonist that binds to α-adrenergic receptors that once activated set off a physiological process in the body that restricts blood supply to the area of the hemorrhoids and thereby reduces swelling in this area. Although very effective, the favorable effects of phenylephrine HCl on hemorrhoids are often masked by the itching and pain in the area around the hemorrhoid(s). To relieve this pain the present invention also includes lidocaine.

To enhance the effects of the ointment of the present invention without adding more than the FDA approved amounts of the active ingredients discussed above a therapeutic effect amount of *Vitis Vinifera* (Grape) skin/seed/leaf extract and aloe *Barbadensis* leaf juice extract are added to the ointment. These homeopathic remedies are not regulated by the FDA and can be safely used in combination with phenylephrine HCl and lidocaine to enhance the potency and extend the period of effectiveness of the ointment of the present invention. The effects of each homeopathic ingredient are further described below.

Red grapevine skin/seed/leaf, *Vitis vinifera*, are rich in flavonoids including anthocyanins, oligomeric proanthocyanidins (OPCs), quercetin and isoquercitrin and have astringent and other homeopathic properties. Clinical trials have proven the efficacy of preparations made from *Vitis vinifera* skin in the treatment of venous insufficiency. Daily doses of 360 and 720 mg of grape leaf extract were confirmed to be safe and effective in the treatment of mild chronic venous insufficiency, reducing significantly lower leg edema and circumference whilst improving other chronic symptoms to a clinically relevant extent. The edema reduction is at least equivalent to that reported for compression stockings and/or other edema-reducing agents. The higher dose was as well tolerated as the lower dose but resulted in a slightly greater and more sustained improvement.

As stated above, grape leaves contain a wide range of polyphenol flavonoids including flavon (op-glycosides and glucuronides, quercetin-3-O-beta-D-glucuronide (main flavonoid), isoquercitrin, anthocyanins, oligomeric proanthocyanidins, catechin, epicatechin monomers and dimers; gallic acid and astilbine. The phytoalexin trans-resveratrol, another polyphenolic substance belonging to the stilbene group, can also be found in grape leaves. In grape leaves, also organic acids appear, mainly malic and oxalic acid but also tartaric acid; citric, fumaric and succinic acid can be detected in the leaves only in traces. It is these components of the grape leave extract that reduces swelling and compliments the active ingredient phenylephrine HCl. Since they have a different mode of phyicloical operation than phenylephrine HCl they last for a longer period of time than phenylephrine HCl thereby extending the effectiveness of the ointment of the present invention.

In addition to these ingredient, the ointment of the present invention also includes aloe *Barbadensis* leaf juice extract that is another homeopathic ingredient that complements the ingredients in the ointment of the present invention. This is effective in further reducing inching and soothing the area around the hemorrhoid(s). The aloe extract is an astringent that helps to heal open wounds and therefore aids in reducing bleeding and itching often associated with hemorrhoids and related conditions.

The ointment of the present invention combines both conventional medical compositions such as phenylephrine HCl and lidocaine with homeopathic compositions such as grape leave and aloe extract to produce an ointment that is more portent for treating hemorrhoids and related conditions than creams that use conventional ingredient or homeopathic ingredients alone. In addition, the overlapping of ingredients that has cumulative and complementary affects aids in prolonging the therapeutic affects of the claimed ointment as compared to other creams for treating hemorrhoids available on the market today. That is, the claimed ointment contains the maximum amount of phenylephrine HCl and lidocaine allowed under the FDA guidelines for topical creams and enhances this by adding two very potent homeopathic ingredients. These homeopathic ingredients enhance the potency of the claimed ointment as well as extend the duration of effectiveness.

The compositions of the present invention are typically administered in a therapeutically effective amount. It will be understood, however, that the amount of the compound actually administered will be determined by a physician, or in reference to a size and height chart provided on the packaging to aid the patient to determine the proper amount that should be used in each treatment. That is the chart will take into account the condition to be treated, the chosen route of administration, the actual compound administered and its relative activity, the age, weight, and response of the individual patient, the severity of the patient's symptoms, and the like. Suitable doses for producing local anesthesia in a mammal range from about 5 mg to about 1000 mg per dose.

One embodiment of the ointment of the present invention comprises about 3% by weight to about 10% by weight of lidocaine and about 0.15% to about 1.25% of phenylephrine HCl. In a preferred embodiment, the ointment comprises about 5% by weight of lidocaine and about 0.25% by weight of phenylephrine HCl as active ingredients and *Vitis Vinifera* (Grape) skin/seed/leaf extract and aloe *Barbadensis* leave juice extract as homeopathic ingredients. The ointment may also comprise additional non-active components including benzyl alcohol, carbomer, cholesterol, hydrogenated lecithin, isopropyl myristate glycol, triethanolamine, Vitamin E Acetate, and purified water, fragrances, coloring agents, vitamins, oils, stability agents and other ingredients necessary to maintain the effectiveness of the ointment.

The carbomer polymers of the ointment are used as thickening, dispersing, and emulsifying agents. They are also used to control the release of medicaments from time-release tablets or from entrapped systems. Carbomers are largely insoluble in water and in the majority of common solvents. When neutralized (with bases, e.g., hydroxides or amines), Carbomers can be soluble in water, alcohol and glycerin. Carbomers are hygroscopic in nature, swelling to many times their original volume when in contact with a solvent. Such swollen particles remain discrete in various mucilaginous or colloidal dispersions. Although swelling is inherently caused by their hydrophilic nature, "maximum volume swell" does not typically occur in water until the polymers are converted to partial organic or inorganic salts. The increased volume is generally stable at all pH levels, but increases as neutralization increases. Maximum volume occurs at 50-90% neutralization, with a neutralization of 75% normally occurring at pH 7.0.

One embodiment of the present invention is directed to a hemorrhoid treating cream composition comprising an effective amount of phenylephrine HCl for relieving swelling, burning, pain, and itching caused by hemorrhoids, an anesthetic effective amount of lidocaine; at least one selected from the group consisting of *Vitis Vinifera* (Grape) skin, *Vitis Vinifera* (Grape) seed and *Vitis Vinifera* (Grape) leaf extract, *Barbadensis* leaf juice extract, *Aloe* and Vitamin E and at least one additive selected from the group consisting of benzyl alcohol, carbomer, cholesterol, hydrogenated lecithin, isopropyl myristate glycol, triethanolamine, aluminum hydroxide gel, calamine, cocoa butter, cod or shark liver oil, starch, white petroleum, wool alcohol, zinc oxide, vegetable or castor oil, polyethylene glycol, and propylene glycol.

The hemorrhoid treating cream composition may also include protectives selected from the group consisting of up to about 50% by weight Aluminum hydroxide gel, up to about 50% by weight. Cocoa butter; Glycerin in a 20- to 45-percent (weight/weight) aqueous solution so that the final product contains not less than 10 and not more than 45 percent glycerin (weight/weight); up to about 50% by weight glycerin in combination with up to about 50% of at least one of the following compounds Hard fat; Kaolin; Lanolin; Mineral oil, Petrolatum, Topical starch and White petrolatum and combinations thereof. Also include in the composition can be astringents selected from the group consisting of about 5 to about 25% by weight of calamine, about 10 to about 50% by weight of witch hazel, about 5 to about 25% by weight of zinc oxide and combinations thereof. Finally, the claimed composition may also include additives selected from the group consisting of Grape seed extract, *Eucalyptus* oil Menthol, Ylang-ylang oil and combinations thereof.

The topical cream composition of the present invention is made by mixing the active ingredients and homeopathic ingredients into a pharmaceutically acceptable carrier and adding the other ingredients as well as water in an order that provides a topical cream wherein the activity of the conventional and homeopathic ingredients are maintained. Conventional ointment/cream producing procedures used in the art can also be used to make the ointment composition of the present invention.

For example one method that can be used to produce the water-based topical ointment of the present invention includes the steps of: providing a mixture of aqueous solvent, one or more penetration enhancers, and, optionally, one or more preservatives; adding to the mixture one or more thickeners; adding to the mixture one or more emulsifiers; heating the mixture to at least a temperature sufficient to solubilize or melt the one or more thickeners and/or one or more emulsifiers; adding phenylephrine HCL and lidocaine as well as the grape leave extract and aloe extract; and adjusting the pH of the mixture to from about 4 to about 6 with a pH-adjuster.

In a further aspect, the pH is adjusted before or during one or more of the providing, adding, and heating steps. In a yet further aspect, the pH is adjusted after the providing, adding, and heating steps. In one aspect, the ointment comprises at least about 60% aqueous solvent by weight. Typically, the mixture is provided as a uniform suspension (dispersion) of ingredients. In certain aspects, the mixture can appear as an emulsion or a solution. It is understood that this method is just one method that can be used to make the ointment of the present invention but other methods available in the art can also be used.

Once the ointment is produced it can be provided in a single dosage convenient packaging, a squeezable tube, a wide-mouth jar, saturated on a pad for application or any other suitable storage means.

It is noted that although throughout the specification the composition of the present invention is referred to as "cream" or "ointment" it is understood that the compositions of the disclosed invention can be provided in a form suitable for topical use such as, for example, cream, ointment, lotion, gels and the like. Further, the compositions can be in a form suitable for use in transdermal devices as well such as wipes, clothes, applicators, pads, and other applications including specifically designed under garments that are designed to keep the ointment in place. All of these formulations can be prepared via conventional processing methods as discussed above.

In addition, although hemorrhoids are explicitly discussed throughout the application it is understood that the composition can be used with other anal conditions including but not limited to anal fissures, anal tares, anal scarring and the like.

Finally, it is understood that the ointment of the present invention can be included as part of a kit that contains a hemorrhoid reducing seat as well as instructions for using the seat and applying the ointment thereafter. The present invention is also directed to the method of treating hemorrhoids and related conditions by applying the ointment of the present invention an either alone or after the use of a device to manipulate the location of the hemorrhoid from an external position to an internal position. One type of the device is pressure-applying seat that is designed to apply pressure around the hemorrhoid area so as to cause the hemorrhoids to be reabsorbed by the body. Converting the external hemorrhoid to an internal hemorrhoid does reduce discomfort but, does not eliminate the itching and swelling often associated with this condition. The ointment of the present invention is designed to reduce these symptoms as discussed above.

While the invention has been illustrated and described with respect to specific illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

What is claimed is:

1. A composition consisting of: phenylephrine HCl, lidocaine, at least one anti-inflammatory agent selected from the group consisting of grape skin extract, grape seed and grape leaf extract, *Aloe barbadensis* leaf juice extract, *Aloe*, and Vitamin E and mixtures and combinations thereof, at least one additive selected from the group consisting of benzyl alcohol, carbomer, cholesterol, hydrogenated lecithin, isopropyl myristate glycol, triethanolamine, aluminum hydroxide gel, calamine, cocoa butter, cod or shark liver oil, starch, white petroleum, wool alcohol, zinc oxide, vegetable oil, castor oil, polyethylene glycol, Grape seed extract, *Eucalyptus* oil, Menthol, Ylang-ylang oil and propylene glycol and mixtures and combinations thereof, at least one astringents selected from the group consisting of calamine, witch hazel, zinc oxide and mixtures and combinations thereof, at least one protective selected from the group consisting of 50% by weight aluminum hydroxide gel of said protective, 50% by weight cocoa butter of said protective, and mixtures and combinations thereof, and at least one topical carrier selected from the group consisting of creams, ointments, gel, lotions, foam and mixtures and combinations thereof, wherein said composition and its ingredients are absent of glycerin, said composition is designed for external topical use and application, and said composition is designed for relieving swelling, burning, pain and itching caused by hemorrhoids.

2. The composition of claim 1 wherein said lidocaine is at least 5% of said composition.

3. The composition of claim 1 wherein said lidocaine is from about 3% to about 5% of said composition.

4. The composition of claim 1 wherein said phenylephrine HCl is from about 0.15% to about 0.25% of said composition.

5. The composition of claim 1 wherein said astringents are selected from the group consisting of about 5 to about 25% by weight of calamine, about 10 to about 50% by weight of witch hazel, about 5 to about 25% by weight of zinc oxide, and mixtures and combinations thereof.

6. A composition consisting of: phenylephrine HCl; lidocaine; at least one anti-inflammatory agent selected from the group consisting of grape skin extract, grape seed and grape leaf extract, *Aloe barbadensis* leaf juice extract, *Aloe*, and Vitamin E and mixtures and combinations thereof; at least one protectives selected from the group consisting of from about 50% by weight Aluminum hydroxide gel, and from about 50% by weight Cocoa butter and mixtures and combinations thereof; and at least one topical carrier selected from the group consisting of creams, ointments, gel, lotions, foam and mixtures and combinations thereof, wherein said composition and its ingredients are absent of glycerin, said composition is designed for external topical use and application, and said composition is designed for relieving swelling, burning, pain and itching caused by hemorrhoids.

7. The composition of claim 6 wherein said lidocaine is at least 5% of said composition.

8. The composition of claim 6 wherein said phenylephrine HCl is from about 0.15% to about 0.25% of said composition.

9. A composition consisting of: phenylephrine HCl; lidocaine, said lidocaine is in the amount of 5% of said composition; at least one protective selected from the group consisting of from about 50% by weight Aluminum hydroxide gel, and from about 50% by weight Cocoa butter and mixtures and combinations thereof; and at least one topical carrier selected from the group consisting of creams, ointments, gel, lotions, foam and mixtures and combinations thereof, wherein said composition and its ingredients are absent of glycerin, and said composition is designed for external topical use and application.

\* \* \* \* \*